United States Patent [19]

Ramachandran

[11] Patent Number: 5,268,497
[45] Date of Patent: Dec. 7, 1993

[54] PROCESS FOR THE PRODUCTION OF NITRILES

[75] Inventor: Ramakrishnan Ramachandran, Allendale, N.J.

[73] Assignee: The BOC Group, Inc., New Providence, N.J.

[21] Appl. No.: 840,363

[22] Filed: Feb. 24, 1992

[51] Int. Cl.$^5$ .................. C07C 253/26; C07C 253/24
[52] U.S. Cl. .................................. 558/320; 558/319; 558/323; 558/324; 558/325; 558/326
[58] Field of Search ............... 558/323, 324, 319, 325, 558/320, 326

[56] References Cited

U.S. PATENT DOCUMENTS

| | | | |
|---|---|---|---|
| 3,200,084 | 8/1965 | Callahan et al. | 558/325 X |
| 3,309,395 | 3/1967 | Nohe et al. | 558/323 |
| 3,321,507 | 5/1967 | Ginnasi et al. | 558/324 X |
| 3,338,952 | 8/1967 | Callahan et al. | 558/323 X |
| 3,394,167 | 7/1968 | Palm et al. | 558/323 |
| 3,427,343 | 2/1969 | Callahan et al. | 558/323 X |
| 4,754,049 | 6/1988 | Khoobiar et al. | 558/319 X |
| 4,849,538 | 7/1989 | Ramachandran et al. | 558/319 |

*Primary Examiner*—Joseph P. Brust
*Attorney, Agent, or Firm*—Coleman R. Reap; Larry R. Cassett

[57] ABSTRACT

A process for the production of an ethylenically unsaturated nitrile from a hydrocarbon feed stream comprised of a mixture of an alkene and an alkane by reaction with an oxygen-containing gas and ammonia. The alkene is converted to unsaturated nitrile by reaction with the oxygen and ammonia in the presence of a suitable catalyst in an ammoxidation reactor; the nitrile product is recovered from the product stream; some of the byproduct carbon oxides and some of the inert gas introduced into the system with the reactants are removed from product stream and the remainder of this stream, now rich in unreacted alkene and alkane, and containing the rest of the byproduct gases and inert gases is introduced into a reactor which contains a catalyst that causes alkane contained in the gas stream to convert to the corresponding alkene. The effluent from the dehydrogenation reactor is recycled to the ammoxidation reactor.

10 Claims, 1 Drawing Sheet

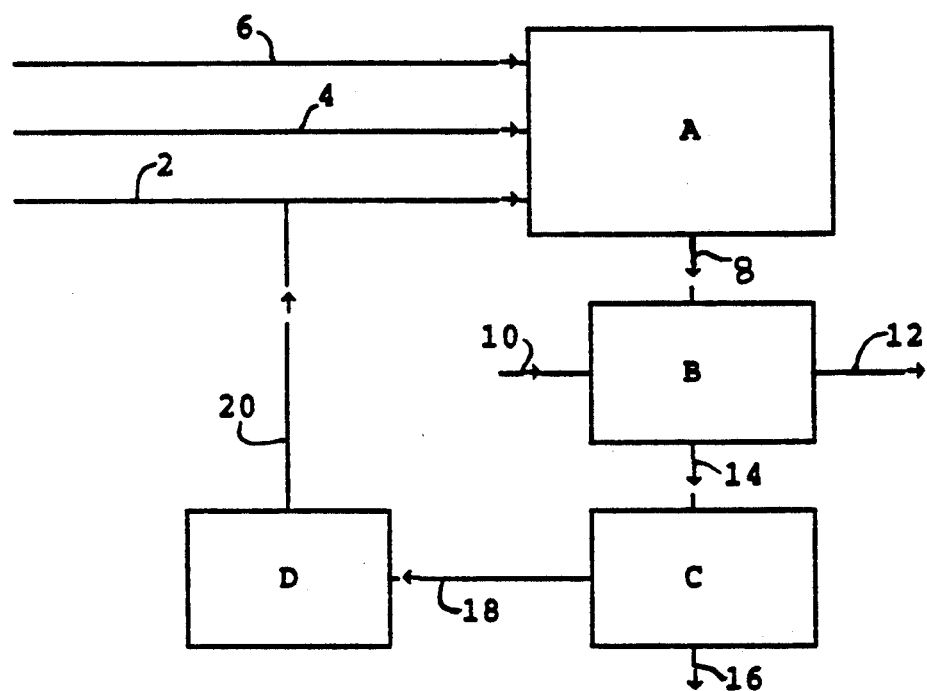

PROCESS FOR THE PRODUCTION OF NITRILES

FIELD OF THE INVENTION

The present invention relates to a process for producing nitriles, and more particularly to a process for producing ethylenically unsaturated nitriles from hydrocarbons, an oxygen-containing gas and ammonia in the presence of an ammoxidation catalyst.

BACKGROUND OF THE INVENTION

The production of nitriles by ammoxidation of an appropriate hydrocarbon in the presence of a suitable catalyst is well known. The production of acrylonitrile, for example, from a gaseous feed of propylene, ammonia and air is described by Bruce E. Gates et al in *Chemistry of Catalytic Processes*, McGraw-Hill (1979), pp. 380-384.

The feed is sent to an ammoxidation reactor where, in the presence of a suitable catalyst, acrylonitrile is produced along with lesser amounts of other nitrogen-containing compounds. The effluent from the ammoxidation reaction is quenched with water and the desired products are obtained in the liquid phase. The gas phase by-products, typically oxygen, carbon dioxide, carbon monoxide and unreacted hydrocarbon, can be combined with natural gas and sent to a boiler for combustion as disclosed, for example, in Yoshino et al., U.S. Pat. No. 3,591,620.

Callahan et al., U.S. Pat. No. 4,335,056, discloses the catalytic ammoxidation of propylene to produce acrylonitrile, followed by the catalytic conversion of propylene in the waste stream to acrylonitrile.

More recently, Khoobiar et al., in U.S. Pat. No. 4,609,502 disclosed a cyclic process for producing acrylonitrile using propane as a starting material. The propane is initially catalytically dehydrogenated in the presence of steam to form propylene. After ammoxidation, the effluent is quenched and the desired product removed, and the off-gases, including propylene and propane, are sent to an oxidation reactor to remove oxygen by selective reaction with hydrogen to form water vapor. The gas mixture exiting the selective oxidation reactor, which contains unreacted propane and propylene, light hydrocarbons and carbon oxides, is treated is in a separator to remove some of the light hydrocarbons and carbon oxides from the gas stream, The propane- and propylene-containing gas stream is then is recycled to the dehydrogenator. A disadvantage of the Koobier et al. process is that it is necessary to remove oxygen from the recycle stream, otherwise the oxygen would degrade the dehydrogenation catalyst.

Ramachandran et al., U.S. Pat. No. 4,868,330, discloses a recycle process for the ammoxidation of propylene with oxygen and ammonia in which, following ammoxidation, the product is removed by quenching, the gas stream is compressed and sent to a separator, such as a pressure swing adsorption (PSA) unit, to remove carbon oxides and propane, and the remaining gas stream, which contains propylene and propane, is recycled to the feed stream. In the process of this patent, propane, which is unreactive, is introduced into the system as a flame suppressor. Propane is a convenient choice for use as a flame suppressor since commercial grade propylene contains propane as an impurity. A disadvantage of the Ramachandran et al process, however is that, since the propane is not reactive in the ammoxidation reactor, it is necessary to continuously remove a portion of the propane entering the system to prevent its buildup therein.

Ramachandran et al. U.S. Pat. Nos. 4,849,537 and 4,849,538 disclose a recycle process for the production of nitriles comprising dehydrogenation of propane to propylene; ammoxidation of the propylene with oxygen and ammonia to produce a product gas stream containing the nitrile product, byproduct carbon oxides, and unreacted propane, propylene and oxygen; removal of the nitrile from the product gas stream by quenching; removal of some of the carbon oxides from the nitrile-free gas stream by PSA; removal of oxygen from the gas stream; and recycle of the resulting propane- and propylene-rich gas stream to the dehydrogenator. In U.S. Pat. No. 4,849,537 a multistage reactor is used to dehydrogenate the propane, and propylene product is withdrawn from a reactor stage intermediate the first and last reactor stages while unreacted oxygen is removed by passage of the product gas stream through a reactor stage downstream from the stage from which the propylene is withdrawn. In U.S. Pat. No. 4,849,538, oxygen is removed from the product stream by means of a selective oxidation reactor located between the PSA unit and the dehydrogenator.

The latter two Ramachandran et al. patents provide useful procedures for recovering unreacted propane from the waste product gas streams produced in propane dehydrogenation/ammoxidation plants, thereby avoiding the wasteful use of the propane as fuel. It would be advantageous to provide an efficient process and system for the conversion to ethylenically unsaturated nitriles of alkane impurities contained in a hydrocarbon feed stream to an alkene ammoxidation reactor. The present invention accomplishes this result and thus permits the use of an alkene feed stream containing an alkane impurity as feed for an alkene ammoxidation reactor.

SUMMARY OF THE INVENTION

The process of the invention comprises the production of nitriles by contacting a hydrocarbon feed containing an alkene and an alkane having at least two carbon atoms with an oxygen-containing gas and ammonia in a gas phase amoxidation reactor in the presence of a catalyst which, under the conditions prevailing in the reactor, causes the alkene to react with the oxygen and ammonia present in the reactor to produce the desired unsaturated nitrile product, but which has no substantial effect on the alkane present in the feed. The ammoxidation reactor product stream, which now contains, in addition to the nitrile product, unreacted alkene, the alkane, oxygen, carbon oxides, nitrogen and argon (if air is used as the oxygen-containing gas) and various other gaseous components in minor amounts, is next processed in a nitrile recovery unit wherein the nitrile is recovered from the product stream by any suitable procedure. The gaseous effluent from the nitrile recovery unit is then treated in a suitable selective separator to remove at least part of the carbon oxides and other gaseous inert components. The gas stream remaining after removal of these components, now containing most of the unreacted alkene and the alkane and some of the carbon oxides and other gaseous components, is introduced into a dehydrogenation reactor wherein some or all of the alkane contained in the gas stream is converted to alkene. The effluent from the dehydrogenation reactor is recycled to the ammoxidation reactor.

In a preferred embodiment of the process of the invention the alkene is propylene, i-butylene or a mixture thereof, these reactants producing acrylonitrile, methacrylonitrile or a mixture thereof, respectively. In another preferred embodiment the hydrocarbon feed contains substantially a single alkane and a single alkene and the alkane and alkene have the same number of carbon atoms and have the same isomeric configuration. In another preferred embodiment the oxygen-containing gas is air. In another preferred embodiment the catalyst in the ammoxidation reactor is a supported mixed oxides of bismuth and molybdenum, uranium and molybdenum, iron and antimony or mixtures of these, and the catalyst in the dehydrogenation reactor is a supported noble metal catalyst, such as palladium or platinum on alumina. In another preferred embodiment the selective separator is a PSA unit and the adsorbent contained therein is an adsorbent which selectively adsorbs alkanes and alkenes.

Another aspect of the invention comprises the system in which the process of the invention is carried out. This system comprises a gas phase ammoxidation reactor having one or more reactor feed inlets and an ammoxidation product outlet; a nitrile recovery unit having a feed inlet connected to the ammoxidation reactor outlet, a nitrile product outlet and a waste gas outlet for the remaining components of the first ammoxidation product stream; a selective separator having an inlet connected to the waste gas outlet, an outlet for the removal of carbon oxides and inert gaseous components and an outlet for the unreacted alkene- and alkane-containing stream; and a dehydrogenation reactor having a feed inlet connected to the unreacted alkene- and alkane-containing stream outlet of the selective separator and a product outlet connected to the ammoxidation reactor.

BRIEF DESCRIPTION OF THE DRAWING

The sole drawing FIGURE illustrates in a block diagram one embodiment of a system for producing ethylenically unsaturated nitriles in accordance with the process of this invention.

DESCRIPTION OF THE PREFERRED EMBODIMENTS

The hydrocarbon composition used as feed in the process of the invention is a mixture generally comprised predominantly of one or more alkenes and smaller amounts of one or more alkanes. Although any alkene and alkane or mixture of alkenes and alkanes that will react under the specified conditions to produce the desired ethylenically unsaturated nitrile or mixture of nitriles can be used as the hydrocarbon feed, it is preferred that alkenes and alkanes having 2 to 6 and preferably 3 to 4 carbon atoms be used as feed. The most preferred alkenes are propylene and i-butylene, and the most preferred alkanes are propane and i-butane. The invention is especially useful for the preparation of a single unsaturated nitrile from a hydrocarbon feed comprising an alkene and an alkane having the same number of carbon atoms and the same isomeric structure. For example, when acrylonitrile is to be produced, the hydrocarbon feed mixture will preferably substantially comprise propylene and propane, and when methacrylonitrile is to be produced, the feed mixture will preferably substantially comprise i-butylene and i-butane. Commercial grade propylene and i-butylene, which contain small amounts of propane and i-butane, respectively, as impurities, are preferred hydrocarbon feed sources, since these gases are inexpensive compared to pure propylene and pure i-butylene. The specific hydrocarbon mixture used in the reaction will, of course, depend upon which nitrile is to be produced. The process of the invention will be described with particular reference to the manufacture of acrylonitrile from propylene and propane, but the invention is not limited thereto.

The amount of alkane contained in the predominantly alkene hydrocarbon feed is not critical; however the process of the invention is more efficient when the alkene constitutes at least about 80% by volume of the feed mixture. In the preferred embodiment of the invention the alkene comprises at least about 90% by volume of the hydrocarbon feed, and in the most preferred embodiment it comprises at least about 95% by volume of the hydrocarbon feed.

The oxygen-containing gas used in the invention may be air, oxygen-enriched air, other oxygen-inert gas mixtures or substantially pure oxygen. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. Air and oxygen-enriched air are preferred sources of oxygen, since these gases are significantly less expensive than high purity oxygen and the nitrogen contained in these gases acts as a flame supressor.

According to one embodiment of the process of the invention, a hydrocarbon mixture containing the desired alkene and alkane or mixture of alkenes and alkanes is contacted in the gaseous state with an oxygen-containing gas and ammonia in a reactor that contains a catalyst which causes the alkene to undergo ammoxidation with oxygen and ammonia but which has substantially no effect on the alkane, at reaction conditions suitable to produce a gaseous product stream containing the desired olefinically unsaturated nitrile as the principal product, carbon monoxide and carbon dioxide as by-products, unreacted alkene and oxygen, the alkane contained in the hydrocarbon feed, and various other components, such as nitrogen and argon (present when air or oxygen-enriched air is used as the source of oxygen) and small amounts of water vapor. Following the ammoxidation reaction, the unsaturated nitrile is recovered from the gaseous product stream in a nitrile product recovery unit. The nitrile-free gas stream is then sent to a separator to remove part of the carbon oxides, nitrogen and argon (if present) and other light components to prevent these from building up in the reaction system. After removal of these components, the residual gas stream, now containing unreacted alkene and alkane and the remainder of the carbon oxides, nitrogen, etc., is sent to a gas phase reactor which contains a catalytic agent that causes a part or all of the alkane contained therein to undergo dehydrogenation to the corresponding alkene. The effluent from the dehydrogenation reactor is then recycled to the alkene ammoxidation reactor for conversion of the newly produced alkene to unsaturated nitrile.

The invention can be better understood from the accompanying drawing. Auxiliary equipment, including compressors, heat exchangers and valves not necessary for an understanding of the invention, have been omitted from the drawing to simplify discussion of the invention.

Turning now to the drawing, the system of the invention includes an alkene ammoxidation reactor A, an unsaturated nitrile recovery unit, B, a hydrocarbon separator, C and a dehydrogenation reactor, D.

Reactor A may be any suitable amoxidation reactor but it is usually of the fixed, moving, fluidized, slurry or transport catalyst bed design. Reactor A may be equipped with heat exchange means (not shown) to remove heat developed in the reaction, which is exothermic. The specific design details of suitable reactors are well known and they form no part of the present invention.

Reactor A contains a catalyst that is highly selective for the preparation of ethylenically unsaturated nitriles from alkenes. Any of the well known catalysts for oxidizing alkenes to nitriles under the specified conditions can be used in the process of the invention. Suitable catalysts for use in the first ammoxidation reactor include mixed oxides of bismuth and molybdenum, iron and antimony, bismuth and antimony, uranium and antimony, and the like. Other suitable catalysts are disclosed in *Chemistry of Catalytic Processes*, Gates et al, McGraw Hill (1979), pp 349-350, and Yoshino et al, U.S. Pat. No. 3,591,620, both of which are incorporated herein by reference. These catalysts may be precipitated on silica, and their use is conventional and well known to those skilled in the manufacture of nitriles. The specific alkene ammoxidation catalysts used in the process of the invention do not form a critical part of the invention. The catalyst selected for use in reactor A may, during the course of the process, also convert a small amount of the alkane present in the hydrocarbon feed to unsaturated nitriles, but this conversion is only incidental, and this catalyst is not intended for such purpose.

On its inlet side alkene ammoxidation reactor A is provided with a fresh hydrocarbon feed line, 2 an oxygen component feed line, 4 and an ammonia feed line, 6. As further discussed below, these reactants may be combined and introduced into reactor A through a single feed line, if desired. On its product discharge side reactor A communicates with unsaturated nitrile recovery unit B through nitrile recovery unit feed line 8.

Nitrile recovery unit B may be any unit suitable for the removal of unsaturated nitriles from a gas stream, such as a condenser or a liquid gas scrubber. When nitrile recovery unit B is a gas scrubber, i.e. an absorber, it is usually of the packed bed design, and it is here illustrated as equipped with a line, 10, for supplying water or an aqueous or nonaqueous liquid into unit B for contact with the product gas entering this unit from reactor A. Unit B is also provided with a nitrile product removal line, 12. Unit B communicates with separator C through gaseous effluent line 14.

The principal purpose of separator C is to prevent buildup in the system of carbon dioxide, carbon monoxide, nitrogen and other generated byproduct gases and inert gases introduced into the system. This unit can be any device which will accomplish this result. Separator C is usually an adsorber, an absorber or a membrane separation unit, and it may comprise a single separator or a train of separators. In preferred embodiments of the invention, separator C is a pressure swing adsorption (PSA) unit or a temperature swing adsorption (TSA) unit. In the most preferred embodiment, it is a pressure swing adsorption unit.

PSA is a well known process for separating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out at superatmospheric pressure, it can run at atmospheric pressure, in which case the desorption will be carried out under vacuum. It is the difference in pressure between the adsorption and desorption stages which is essential for operation of the system.

When separator C is a PSA unit, the adsorbent contained therein may be any art-recognized material which adsorbs alkenes and alkanes to a substantially greater degree than carbon oxides, nitrogen and argon. By proper selection of the adsorbent, the operation of the PSA unit can be readily controlled utilizing art-recognized manipulations so that the recycle stream formed therein contains a substantial portion of the alkene and alkane and lesser percentages of carbon oxides nitrogen and other inert gases. Silica gel and zeolite molecular sieves are preferred adsorbent materials, and silica gel is the most preferred adsorbent.

Separator C is provided with a waste gas discharge line, 16, and a recycle line 18, the latter of which is connected to ammoxidation reactor D.

Dehydrogenation reactor D may be any reactor suitable for the dehydrogenation of alkanes to alkenes. The specific design details of suitable reactors are well known and form no part of the present invention. Since the amount of alkane entering the reactor A in the hydrocarbon feed stream is generally small, reactor D may be a small dehydrogenation unit. Typical dehydrogenation reactors are described in the above-mentioned U.S. Pat. Nos. 4,609,502, 4,849,537 and 4,849,538, the disclosures of which are incorporated herein by reference.

According to one embodiment of the invention, reactor D can comprise a pair of units arranged in parallel and operated out of phase, so that when one reactor is in service the other is being regenerated. When the efficiency of the reactor in service drops to a predetermined level, it can be taken out of service and regenerated while the newly regenerated reactor it put into service.

The catalyst used in reactor D may be any catalyst which effects the dehydrogenation of alkanes under the conditions prevailing in reactor D. Typical catalysts and reaction conditions are also described in the above-mentioned U.S. Pat. Nos. 4,609,502, 4,849,537 and 4,849,538. Suitable catalysts include supported or unsupported Group VIII noble metal catalysts, such as platinum on an alumina support, used with or without promoters. As is the case with the design of reactor D, the particular dehydrogenation catalyst used is not critical and forms no part of the invention.

In the embodiment illustrated in the drawing, reactor D is provided with a product discharge line, 20, which communicates with hydrocarbon feed line 2.

According to the embodiment of the process of the invention illustrated in the drawing, a hydrocarbon feed stream comprising the desired alkene and alkane enters reactor A through inlet line 2. Simultaneously an oxygen-containing gas stream and gaseous ammonia are introduced into reactor A through lines 4 and 6, respectively. In a variation of this arrangement, the hydrocarbon, oxygen-containing gas and gaseous ammonia may by combined and the gaseous mixture introduced into reactor A through a single inlet line. The particular inlet arrangement used is a matter of choice and it will generally depend upon the type of reactor used for practicing the invention. In fixed bed reactor systems the components of the feed are often mixed before they enter the reactor and are thus fed into the reactor through a single line, whereas in fluidized bed reactor systems, the components are often separately fed into the reactor.

The feed gases entering reactor A contact the catalyst and react to form the desired ethylenically unsaturated nitrile. The conditions of the hydrocarbon ammoxidation are well known and form no part of the invention. Typically, the ammoxidation reaction is conducted at high temperatures, typically in the range of about 250° to 600° C., and usually in the range of about 300° to 500° C., and at low pressures, typically in the range of about 2 to 50 psig, and usually in the range of about 3 to 30 psig. The reactants are generally passed through the reactor at a velocity in the range of from about 0.5 to 5 ft/sec. The ratios of oxygen to hydrocarbon and ammonia to hydrocarbon in the feed are generally in the ranges of about 0.3:1 to 10:1 and about 0.8:1 to 1.3:1 by volume, respectively.

The amount of unreacted alkene present in the gaseous effluent from reactor A will depend in part on the percent per-pass conversion of the alkene entering the ammoxidation reactor which is converted to products. Those skilled in the art will appreciate that factors such as choice of catalyst, operating pressures and the like can be adjusted to have the ammoxidation reactor operate at a desired conversion of alkene in the feed thereto. At lower operating conversions, e.g. 60 percent conversion, there will be a greater amount of unreacted alkene leaving reactor A. For example, using substantially pure oxygen in an ammoxidation reactor operating at 80 percent conversion in accordance with the invention, there will be only about 10 to 15 percent unreacted alkene in the Reactor A effluent whereas, at 60 percent conversion, there will be a greater percentage of unreacted alkene in the reactor A effluent.

The product gas stream leaving reactor A contains the nitrile as the main product, and carbon dioxide and carbon monoxide as byproducts. As noted above, the product stream generally also contains unreacted alkene and oxygen, the alkane, which does not undergo appreciable reaction in reactor A, and small amounts of other byproducts, impurity gases and nonreactive gases, such as nitrogen, argon and saturated hydrocarbons, e.g. methane. The product gas stream leaves reactor A via line 8 and preferably passes through a heat exchanger (not shown) wherein it is cooled to a temperature in the range of about 30 to about 200° C. The cooled product gas stream enters nitrile removal means B, in which the nitrile product is removed from the gas stream. When scrubbing is the method of recovery employed, the solvent, which may be water, dissolves substantially all of the nitrile in the product gas stream, and the nitrile-containing solution exits scrubber B via line 12. It is usually further treated to recover the nitrile as a substantially pure product. The scrubbed gas stream leaves nitrile removal means B through line 14 and enters separator C.

As noted above, separator C serves to prevent the buildup of carbon dioxide, carbon monoxide, nitrogen and other generated byproduct gases and inert gases in the system. It is preferred to remove only those amounts of carbon oxides and inert gases (nitrogen and argon) in excess of the amounts of these gases necessary to maintain a nonflammable atmosphere in the system, so that the process can be optimized. To accomplish this, it is only necessary to remove amounts of carbon oxides equal to the amounts of these byproducts produced in reactor A in each pass and amounts of inert gases (nitrogen, argon unreactive hydrocarbons, etc., equal to the amounts of these components introduced into reactor A in the feed streams.

Although separator C can be operated at ambient pressure, it is sometimes preferable to operate this unit at superatmospheric pressures. This is particularly the case when separator C is a PSA unit. When it is desired to operate separator C at elevated pressures, this can be accomplished by passing the gaseous effluent from nitrile recovery unit B through a compressor or other suitable means (not shown) to increase the pressure thereof to the preferred operating pressure, which in the case of a PSA unit, is typically in the range of about 3 to 50 psig, and preferably in the range of about 20 to 40 psig. The range of preferred operating pressures will depending on the adsorbent utilized.

A portion of the nitrogen and carbon oxides and all or a part of the oxygen entering separator C through line 14 are withdrawn from the system through line 16. These waste gases are preferably combusted and/or vented. If desired, oxygen may be recovered from the vent stream and recycled to the feed to the reactors to enhance the operation of the system. The gases not discharged from the system through line 16 are sent through line 18 to reactor D, wherein some or all of the alkanes in the incoming gas stream is dehydrogenated to corresponding alkenes.

The alkanes contained in the gas stream entering reactor D through line 18 contact the catalyst contained therein at suitable reaction conditions and undergo dehydrogenation. The alkane dehydrogenation reaction is typically carried out at temperatures in the range of about 400 to about 700° C. and at pressures in the range of about 0.1 to 5 bar, as noted in the above-mentioned U.S. Pat. Nos. 4,609,502, 4,849,537 and 4,849,538. The dehydrogention reaction is generally endothermic; accordingly, it will be desirable to provide means for heating the reactant streams entering reactor D or means for heating the reactor contents (not shown). The dehydrogenation reaction can be operated at low efficiency, since, to maintain equilibrium in the system it is only necessary to convert in each pass an amount of alkane equal to the amount entering the system through hydrocarbon feed line 2.

Oxygen contained in the feed stream to reactor D may eventually reduce the effectiveness of the dehydrogenation catalyst contained in reactor D. While it is not necessary to operate reactor D at high efficiency, degradation of the dehydrogenation catalyst can, to some extent, be reduced by eliminating oxygen from the gas stream entering reactor D. This can be accomplished by removing the oxygen in separator C, as by means of multiple adsorption beds, one of which is effective to separate oxygen from the hydrocarbons being recycled. Alternatively, the oxygen can be caused to react with the hydrogen present in the gas stream, as by passing the gas stream through a selective oxidation reactor of the type described in the above-mentioned U.S. Pat. No. 4,849,538.

It is not absolutely necessary, however, to remove the oxygen from the feed stream to reactor D, since there is no requirement to operate reactor D at high efficiency. Furthermore, the catalyst can be easily regenerated by heating it to burn of accumulated carbon, as described in the above-mentioned U.S. Pat. No. 4,849,537.

It may also be desirable to introduce hydrogen into reactor D to prolong the life of catalyst contained therein, particularly when no means are provided for removing oxygen from the gas stream prior to its entry into reactor D. This can be easily accomplished by recycling some or all of the hydrogen introduced into the recycle stream during previous passes of the gas stream through the dehydrogenation reactor.

The product gas stream from reactor D passes through line 20 and is recycled to reactor A. The effluent from reactor A can be sent directly to reactor A or it can be mixed with fresh hydrocarbon feed entering the system through line 2, as shown in the drawing.

It is within the scope of the present invention to utilize conventional equipment to monitor and automatically regulate the flow of gases within the system so that it can be fully automated to run continously in an efficient manner.

The process of this invention is advantageous in its simplicity, ease of operation, low capital and operating costs as well as providing a substantially reduced flammability potential. The process can be run at a relatively low conversion of the feed hydrocarbon to the desired product to achieve substantially improved selectivity for the desired nitrile product. Selectivity is the amount of desired product divided by the total of all products. It will be appreciated that a system that runs at comparatively low conversion and achieves enhanced selectivity and hence increased overall yield of a desired product utilizing a less expensive grade of feed material, such as commercial grade propylene or i-butene, is highly advantageous.

The invention is further illustrated by the following example wherein, unless otherwise indicated, parts, percentages and ratios are on a volume basis.

EXAMPLE

A vapor phase acrylonitrile production run was simulated in a reactor system similar to the system of FIG. 1, wherein reactor A is a vapor phase fluidized bed reactor packed with mixed iron-antimony oxides supported on silica, reactor D is a vapor phase fixed bed reactor packed with platinum supported on alumina and separator C is a pressure swing adsorber packed with silica gel. The simulated hydrocarbon feed to the system consists of 93% by volume propylene and 7% by volume propane. The feed to the reactor A is comprised of the Fresh Feed component and the Recycle Stream component. The various flow rates and projected results are tabulated in the TABLE.

The propylene conversion and selectivity to acrylonitrile in reactor A is 96% and 78%, respectively. The propane conversion and selectivity to propylene in dehydrogenator D is 40% and 93%, respectively.

This example illustrates the usefulness of the process of the invention in converting a hydrocarbon feed comprised of mixture of an alkane and an alkene to an ethlenically unsaturated nitrile.

TABLE

| Comp | Fresh Feed | AN Reactor Feed | Scrubber Feed | PSA Feed | Dehydro Reactor Feed | Recycle Stream | PSA Vent |
|---|---|---|---|---|---|---|---|
| $C_3H_6$ | 9.8 | 8.4 | 0.3 | 0.5 | 2.4 | 2.3 | 0.1 |
| $C_3H_8$ | 0.7 | 1.3 | 1.2 | 1.8 | 9.1 | 8.7 | 0.2 |
| $NH_3$ | 11.3 | 8.9 | 1.0 | | | | |
| $O_2$ | 24.2 | 19.7 | 3.5 | 5.4 | | 4.6 | 5.6 |
| AN[1] | | | 5.9 | | | | |
| HCN | | | 1.4 | | | | |
| ACR[2] | | | 0.1 | | | | |
| ACN[3] | | | 0.1 | | | | |
| CO | | 0.1 | 0.8 | 1.1 | 0.9 | 0.9 | 1.1 |
| $CO_2$ | | 1.6 | 4.1 | 4.1 | 13.0 | 12.4 | 2.1 |
| $H_2O$ | | 25.5 | | | | | |
| $CH_4$ | | 0.7 | 0.6 | 1.0 | 4.9 | 4.7 | 0.1 |
| $C_2H_4$ | | 0.1 | 0.1 | 0.1 | 0.5 | 0.5 | 0.0 |
| $C_2H_6$ | | 0.1 | 0.1 | 0.1 | 0.5 | 0.5 | 0.0 |
| $H_2$ | | 8.5 | 8.0 | 12.4 | 3.4 | 3.3 | 14.5 |
| $N_2$ | 54.0 | 50.6 | 47.4 | 73.6 | 65.2 | 62.2 | 76.3 |
| Flow rate in Moles | 1249.8 | 1585.0 | 1691.8 | 1090.6 | 197.0 | 206.4 | 884.1 |

AN[1] = Acrylonitrile
ACR[2] = Acrolein
ACN[3] = Acetonitrile

Although the invention has been described with particular reference to a specific experiment, this experiment is merely exemplary of the invention and variations are contemplated. For example, the reaction can be carried out under conditions that will effect the production of other nitriles. Similarly, other catalysts and adsorbents and other means of gas separation can be used in the invention, if desired. Similarly, the process of the invention may be practiced in equipment arrangements other than those illustrated in the drawings. The scope of the invention is limited only by the breadth of the appended claims.

I claim:

1. A process for the production of an ethylenically unsaturated nitrile from a hydrocarbon feed stream at least 90 volume percent of which is comprised of at least one alkene having 3 to 6 carbon atoms and which contains as an impurity at least one alkane having 3 to 6 carbon atoms comprising the steps of:

(a) contacting said feed stream with an oxygen-containing gas and ammonia in a reaction zone in the presence of an ammoxidation catalyst at a temperature and pressure which causes gas phase reaction between alkenes, oxygen and ammonia to produce an ethylenically unsaturated nitrile, thereby producing a gaseous stream comprising an ethylenically unsaturated nitrile, said at least one alkane, unreacted alkene and carbon oxides;

(b) separating said ethylenically unsaturated nitrile from said gaseous stream in a nitrile recovery zone;

(c) separating at least part of said alkane and unreacted alkene from said carbon oxides by pressure swing adsorption or temperature swing adsorption by means of an adsorbent which more strongly adsorbs alkanes and alkenes than carbon oxides;

(d) contacting the separated alkane with a dehydrogenation catalyst at a temperature and pressure which causes at least some of said alkane to convert to the corresponding alkene; and (e) recycling the converted alkene to said reaction zone.

2. The process of claim 1, wherein the oxygen-containing gas is selected from the group consisting of pure oxygen, air and a gas enriched in oxygen relative to air.

3. The process of claim 2, wherein said alkene is selected from propylene, i-butylene and mixtures of these, and said alkane is selected from propane and i-butane and mixtures of these.

4. The process of claim 3, wherein said alkene is propylene and said alkane is propane.

5. The process of claim 3, wherein said alkene is i-butylene and said alkane is i-butane.

6. The process of claim 1, wherein said ammoxidation catalyst is a member selected from the group consisting of bismuth-molybdenum mixed oxides, bismuth-antimony mixed oxides, uranium-molybdenum mixed oxides, iron-antimony mixed oxides and mixtures of these.

7. The process of claim 1, wherein said dehydrogenation catalyst is one or more Group VIII noble metals.

8. The process of claim 1, wherein step (c) is carried out by pressure swing adsorption.

9. The process of claim 8, wherein said pressure swing adsorption is carried out by means of silica gel or a zeolite molecular sieve.

10. The process of claim 1, wherein said nitrile recovery zone comprises a liquid scrubber.

* * * * *